(12) United States Patent
Stark et al.

(10) Patent No.: US 6,827,670 B1
(45) Date of Patent: Dec. 7, 2004

(54) SYSTEM FOR MEDICAL PROTOCOL MANAGEMENT

(75) Inventors: John G. Stark, Minnetonka, MN (US); Duane Oyen, Maple Grove, MN (US); Timothy J. B. Hanson, Plymouth, MN (US); Timothy Tracey, Wayzata, MN (US); Steven Backes, Minneapolis, MN (US); Gary Manninen, Maple Grove, MN (US)

(73) Assignee: IZEX Technologies, Inc., Minneapolis, MN (US)

( * ) Notice: Subject to any disclaimer, the term of this patent is extended or adjusted under 35 U.S.C. 154(b) by 0 days.

(21) Appl. No.: 09/416,192

(22) Filed: Oct. 11, 1999

(51) Int. Cl.[7] .............................................. A63B 21/00
(52) U.S. Cl. ............................. 482/9; 482/8; 482/900
(58) Field of Search ....................... 482/1–9, 900–902

(56) References Cited

U.S. PATENT DOCUMENTS

| | | |
|---|---|---|
| 4,586,495 A | 5/1986 | Petrofsky |
| 4,621,620 A | 11/1986 | Anderson |
| 4,645,199 A | 2/1987 | Bloemendaal |
| 4,653,479 A | 3/1987 | Maurer |
| 4,801,138 A | 1/1989 | Airy et al. |
| 4,825,852 A | 5/1989 | Genovese et al. |
| 4,828,257 A | 5/1989 | Dyer et al. |
| 4,863,157 A | 9/1989 | Mendel et al. |
| 4,909,262 A | 3/1990 | Halpern et al. |
| 4,922,925 A | 5/1990 | Crandall et al. |
| 4,934,694 A | 6/1990 | McIntosh |
| 4,958,632 A | 9/1990 | Duggan |
| 5,003,965 A | 4/1991 | Talish et al. |
| 5,012,820 A | 5/1991 | Meyer |
| 5,052,375 A | 10/1991 | Stark et al. |
| 5,052,379 A | 10/1991 | Airy et al. |
| 5,181,902 A | 1/1993 | Erickson et al. |
| 5,195,941 A | 3/1993 | Erickson et al. |
| 5,209,712 A | 5/1993 | Ferri |
| 5,239,987 A | 8/1993 | Kaiser et al. |
| 5,255,188 A | 10/1993 | Telepko |
| 5,368,546 A | 11/1994 | Stark et al. |
| 5,474,090 A | 12/1995 | Begun et al. |
| 5,484,389 A | 1/1996 | Stark et al. |
| 5,569,120 A | 10/1996 | Anjanappa et al. |
| 5,579,378 A | 11/1996 | Arlinghus, Jr. |
| 5,704,364 A | 1/1998 | Saltzstein et al. |

(List continued on next page.)

OTHER PUBLICATIONS

"Put Your Patient's Recovery Steps Ahead with the Sutter CMP™ 9000", by Sutter Biomedical Inc., SUT 133, V85, Jan. 1985, pp. 1–6.
1994 Thera–Kinetics Product literature.
"Let Your Fingers Do The Talking" by, Fred Hapgood, Boston, Inc, vol. 19, Iss. 17, Nov. 18, 1997, pp. 119–120.

*Primary Examiner*—Glenn E. Richman
(74) *Attorney, Agent, or Firm*—Patterson, Thuente, Skaar & Christensen, P.A.; Peter S. Dardi

(57) ABSTRACT

A system for treating orthopedic injuries by presenting a set of treatment protocols; approving a treatment protocol from among the presented set of treatment protocols; capturing information identifying the approved treatment protocol from among the set of presented protocols; and generating information from the captured information into a form compatible with a handheld computer adapted for connection to an orthopedic sensor system. The generated information includes parameters of the identified approved treatment protocol. The process may also include the steps of basing the presented set of treatment protocols upon a database of historic patients, orthopedic injuries, treatment protocols and outcomes, and retaining information about the current patient, the patient's injury, treatment protocol and outcome.

20 Claims, 14 Drawing Sheets

U.S. PATENT DOCUMENTS

| | | |
|---|---|---|
| 5,751,959 A | 5/1998 | Sato et al. |
| 5,775,332 A | 7/1998 | Goldman |
| 5,801,756 A | 9/1998 | Iizawa |
| 5,823,975 A | 10/1998 | Stark et al. |
| 5,929,782 A | 7/1999 | Stark et al. |
| 5,980,447 A | 11/1999 | Trudeau |
| 6,007,459 A | 12/1999 | Burgess |
| 6,014,432 A | 1/2000 | Modney |
| 6,059,692 A | 5/2000 | Hickman |
| 6,190,287 B1 * | 2/2001 | Nashner ......................... 482/8 |
| 6,206,829 B1 * | 3/2001 | Iliff ............................. 600/300 |
| 6,246,975 B1 * | 6/2001 | Rivonelli et al. ........... 434/262 |
| 6,283,761 B1 * | 9/2001 | Joao ............................ 434/236 |

* cited by examiner

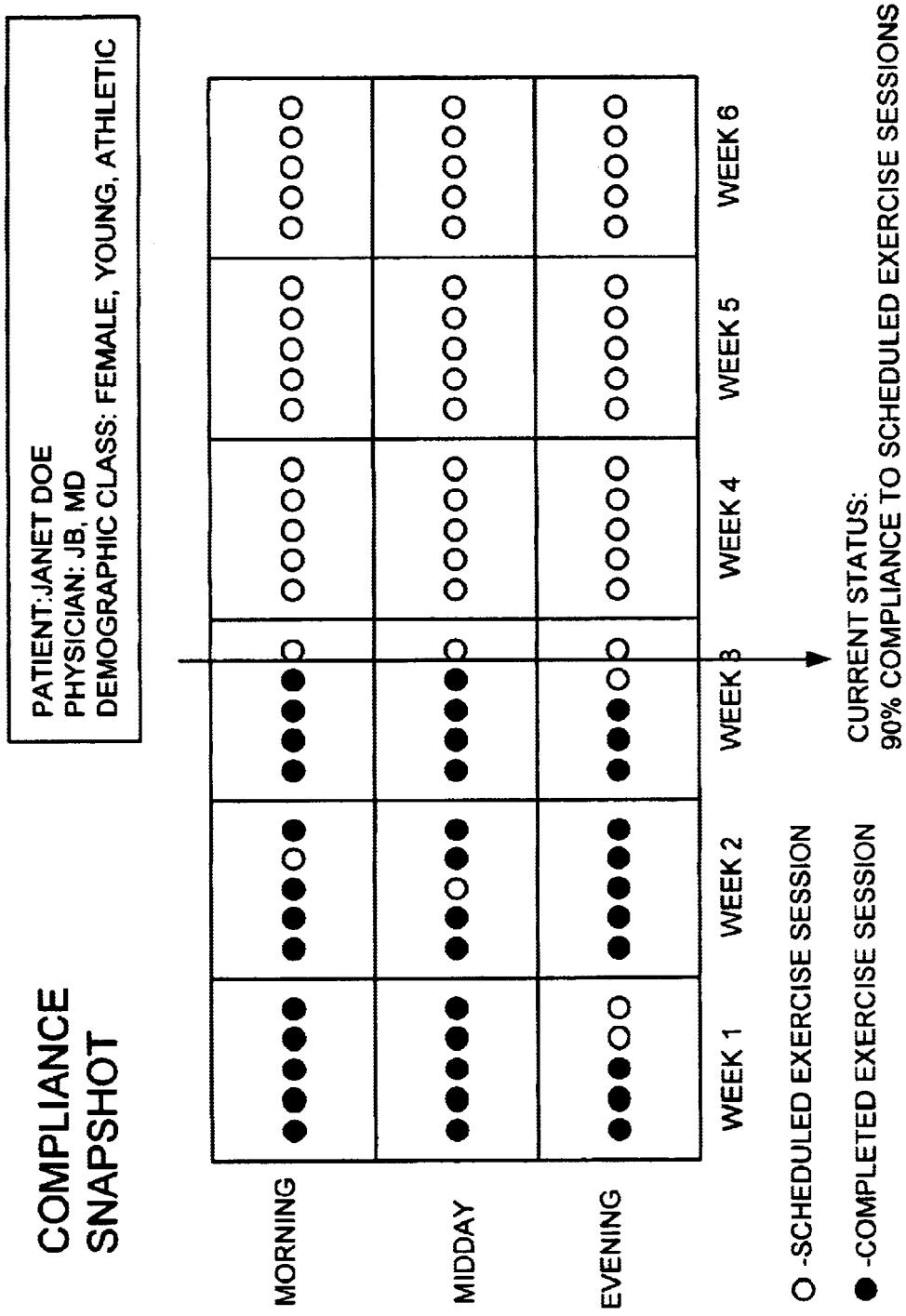

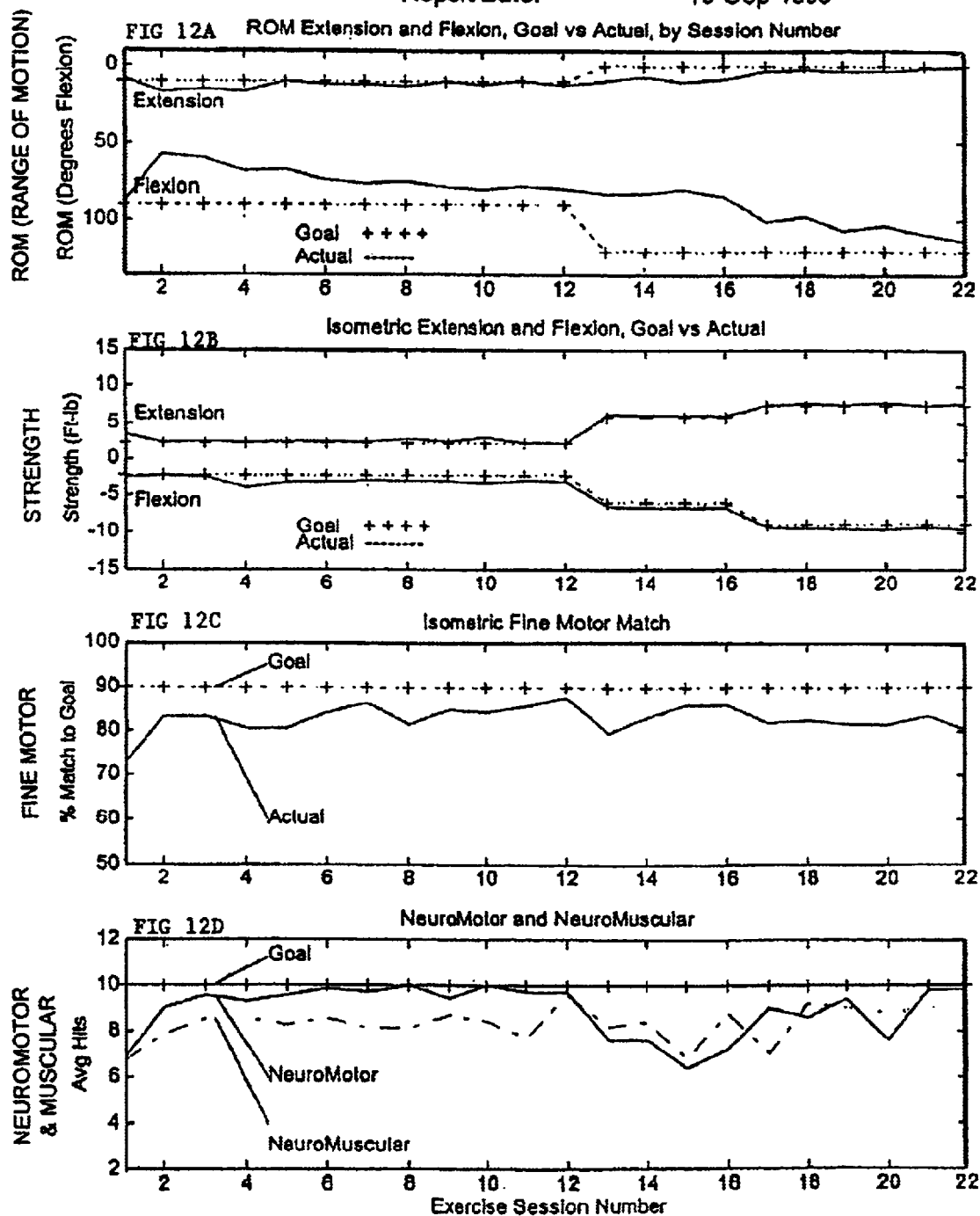

FIGURE 13

RECOVERY GOAL ANALYSIS

PATIENT: JANET DOE
PHYSICIAN: JB, MD
DEMOGRAPHIC CLASS: FEMALE, YOUNG, ATHLETIC

| ACTUAL EXERCISE PERFORMANCE PATIENT INJURED LIMB | BENCHMARK GOAL OR PATIENT CONTRA-LATERAL LIMB GOAL | STATISTICAL HISTORICAL CATEGORY POPULATION |
|---|---|---|
| • ROM: 0-114 | • ROM: 0-128 | • 0-125 |
| • QUAD MVC: 105 FT/LB | • QUAD MVC: 115 FT/LB | • 120 FT/LB |
| • HAM MVC: 122 FT/LB | • HAM MVC: 118 FT/LB | • 123 FT/LB |
| • FINE MOTOR MATCH: 77% AVG. | • FINE MOTOR MATCH: 79% AVG. | • 82% |
| • NEUROMOTOR DIFFICULTY: 100% HITS: 90% | • NEUROMOTOR DIFFICULTY: 100% HITS: 90% | • 100% • 91% |
| • NEUROMUSCULAR DIFFICULTY: 100% HITS 75% | • NEUROMUSCULAR DIFFICULTY: 100% HITS 80% | • 100% • 85% |

ADAPTIVE PROTOCOL DATA ELEMENTS

CHALLENGE LEVEL RATE OVER TIME

SYSTEM FOR MEDICAL PROTOCOL MANAGEMENT

BACKGROUND OF THE INVENTION

Field of Invention

The present invention relates to orthopedic treatment and, in particular, the present invention relates to systems for orthopedic treatment in which patient treatment protocols are reduced to digitalized representations for use in conjunction with portable computerized or digitalized orthopedic treatment devices. The present invention also relates to selection or creation of an appropriate patient treatment protocol, as well as intervention and control to modify the patient treatment protocol. In particular, this aspect of the present invention also relates to modification of a patient treatment protocol when the modification is contingent upon certain events related to feed-back data recorded by a computerized orthopedic treatment device.

Orthopedic treatment historically involved a treatment professional, normally a physician, examining and diagnosing an orthopedic injury in a patient, prescribing a treatment protocol of activities or exercises for the patient to follow in order to facilitate healing, and subsequent re-examination to assess patient progress. Additionally, the patient was traditionally guided and assisted in following the prescribed treatment protocol by other treatment professionals, such as physical therapists, who could inform and advise the attending physician concerning patient compliance with the protocol and communicate and assist with the patient to provide desired activity details and elicit patient response. The traditional treatment path often included either hospitalization or patient visits at a physical therapy facility.

In modern times, financial pressure upon the medical arts and the surrounding medical industry has increased the number of patients each physician must treat and reduced the rate of hospitalization. There is a tendency to employ physical therapy facilities, as well as reduce the direct supervision of the patient activities by the physical therapist. Computerized devices have been developed that at least augment the physical therapist contact, and monitor patient activities under a treatment protocol. One particularly innovative device system, the IZEX sensor-instrumented orthosis and associated hand-held Smart IDEA™ computer/communicator, not only replaces some of the physical therapist's function of (1) advising and instructing the patient and (2) advising the attending physician of patient outcome and compliance, but also allow an improved (quantitative) measuring and monitoring of patient rehabilitation activities and exercise parameters, such as effort exerted in rehabilitation exercises or stress applied to the orthopedic injury. This improved monitoring enables exploitation of a long observed and literature-documented phenomenon of improved recovery in response to appropriately applied exercises to orthopedic injuries. The topic of accelerated and improved recovery through the use of controlled bio-feedback based rehabilitation has been reviewed extensively by one of the present inventors in patents U.S. Pat. No. 5,052,375; U.S. Pat. No. 5,368,546; U.S. Pat. No. 5,484,389; U.S. Pat. No. 5,823,975; and U.S. Pat. No. 5,929,782 and the entire disclosures of these patents are incorporated herein by reference.

In spite of advances such as the IZEX SmartIDEA™, the ultimate goal of efficiently achieving an optimal yet accelerated recovery outcome has remained elusive. This is, at least in part, because the utilization of the IZEX™ orthosis brace system and SmartIDEA™ computer/communicator previously have continued to rely upon a treatment professional performing an examination, generating a diagnosis and subsequently providing a treatment protocol for the injured patient. The SmartIDEA™ hand-held computer was then programmed based upon the protocol. The treatment professional may not readily know nor have available information concerning the optimal treatment protocol for an accurately diagnosed injury. It would be a significant advance in orthopedic treatment if a physician or other treatment professional could be rapidly advised concerning optimal treatment information based upon up-to-date experiential outcomes of similar treated injuries. It would also be a significant advance if the physician or treatment professional could leverage their own expertise and their colleagues'most recent knowledge to appropriately modify and adapt previously successful protocols for a new patient. It would also be a significant advance if the protocol could be installed in a handheld computer (monitoring device/computer/ communicator) device with ease and efficiency. Additionally, it would be a significant advance to allow appropriate progress-based and time-based modification of the patient's protocol. Modification may be best thought of as intervention. Intervention, most particularly real-time modification, into rehabilitation exercise protocols by a patient or in response to a patient request or by a treatment professional or by an automated computer algorithm, where such modification is limited by reasonable constraints, would also offer further progress toward the goal of efficiently achieving an optimal, yet accelerated, orthopedic recovery outcome. A system which provides real-time intervention can also allow delayed intervention. Intervention can be initiated by the patient, by the treatment professional, or by the automated computer system. The following system provides such advances to the orthopedic arts.

BRIEF DESCRIPTION OF THE FIGURES AND APPENDICES

Figure 7:
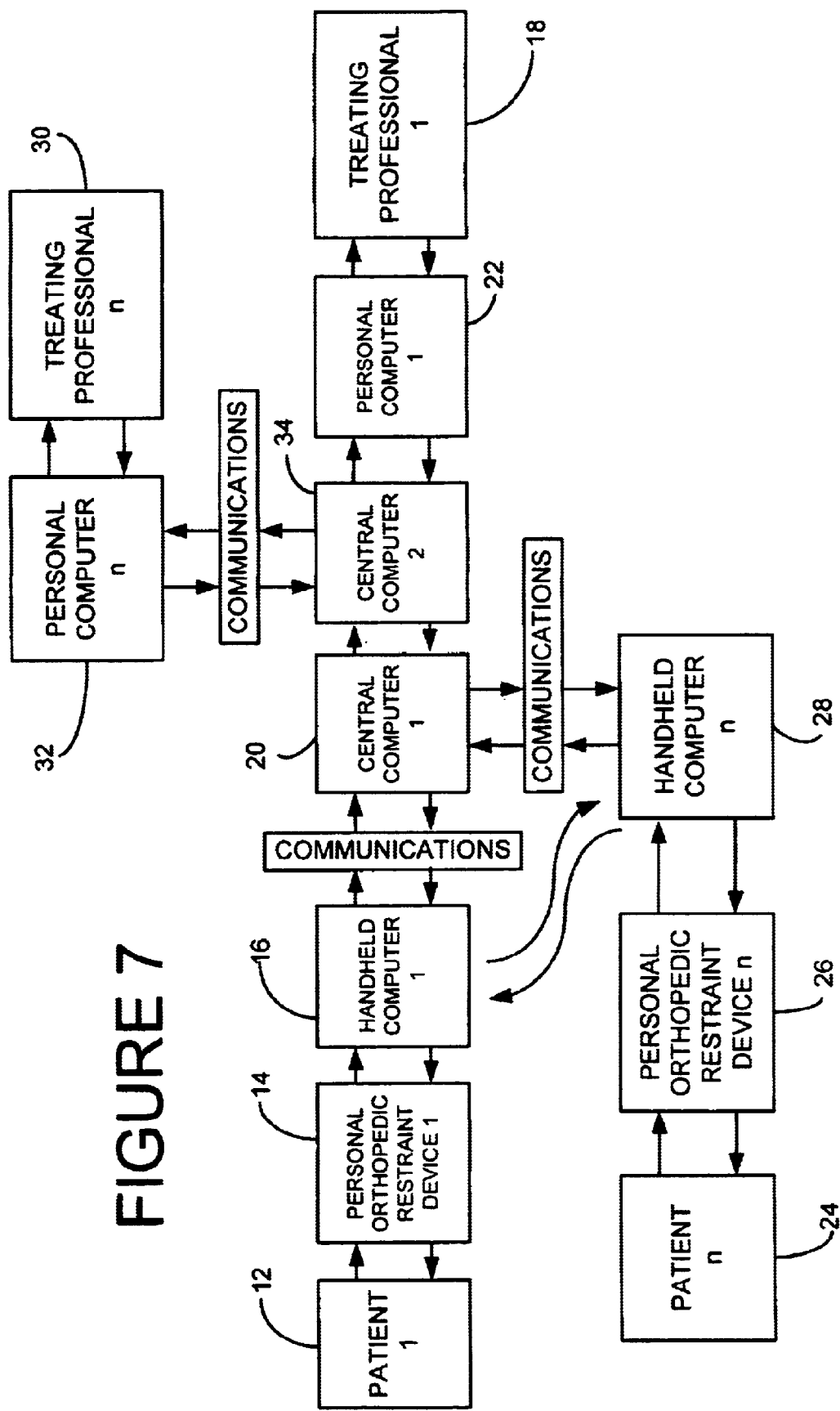
Figure 8:
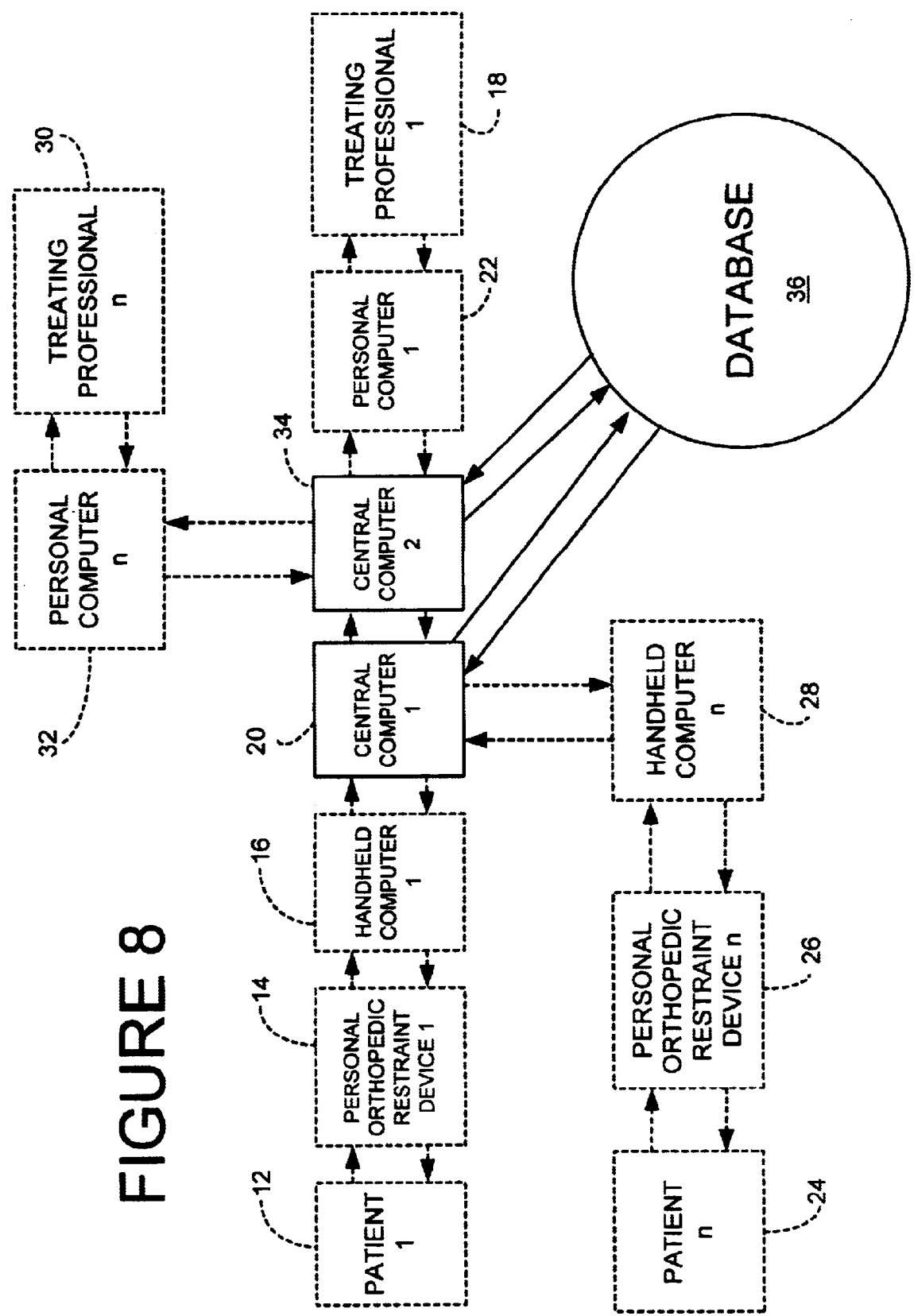
Figure 9:
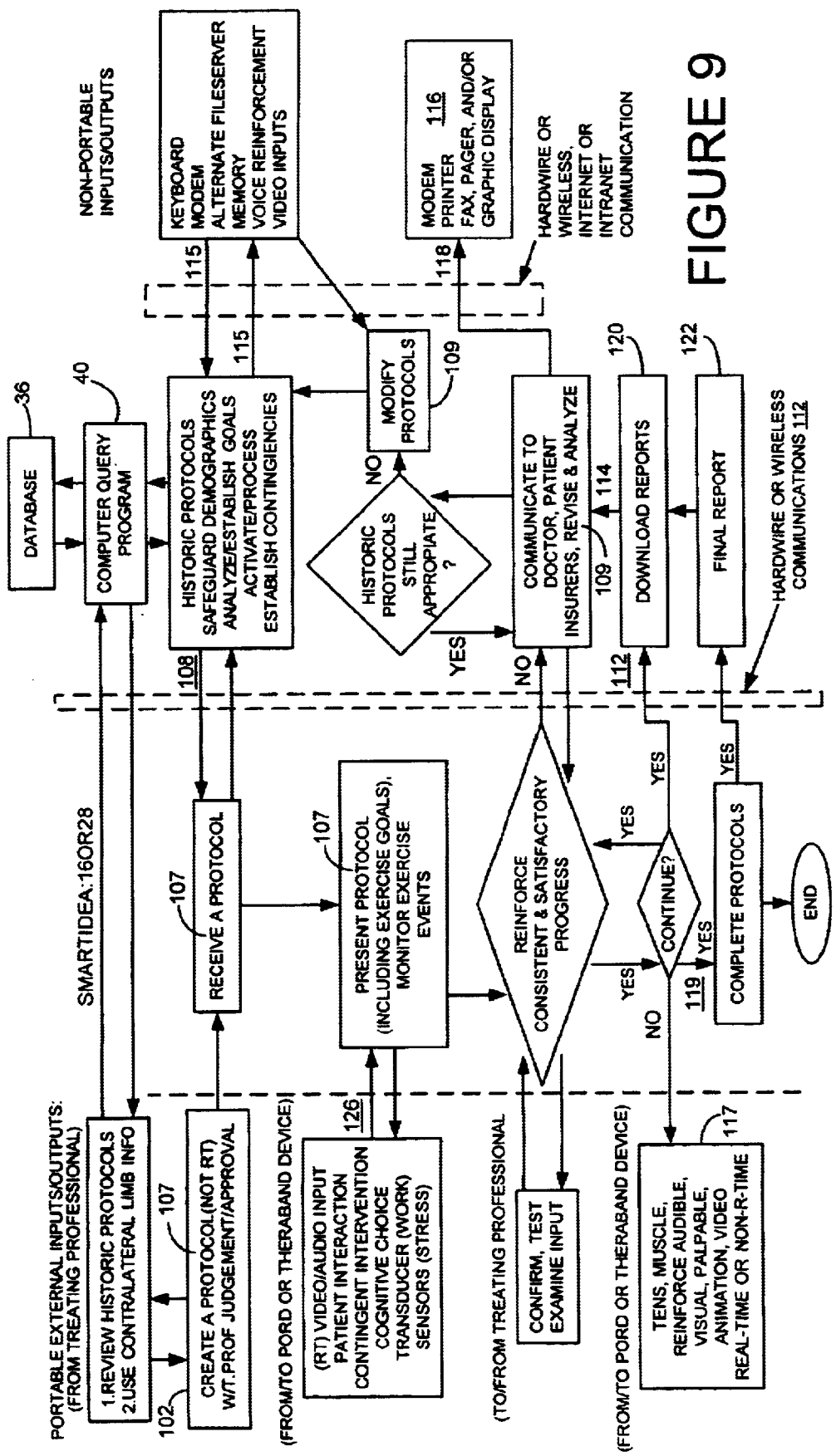
Figure 10:
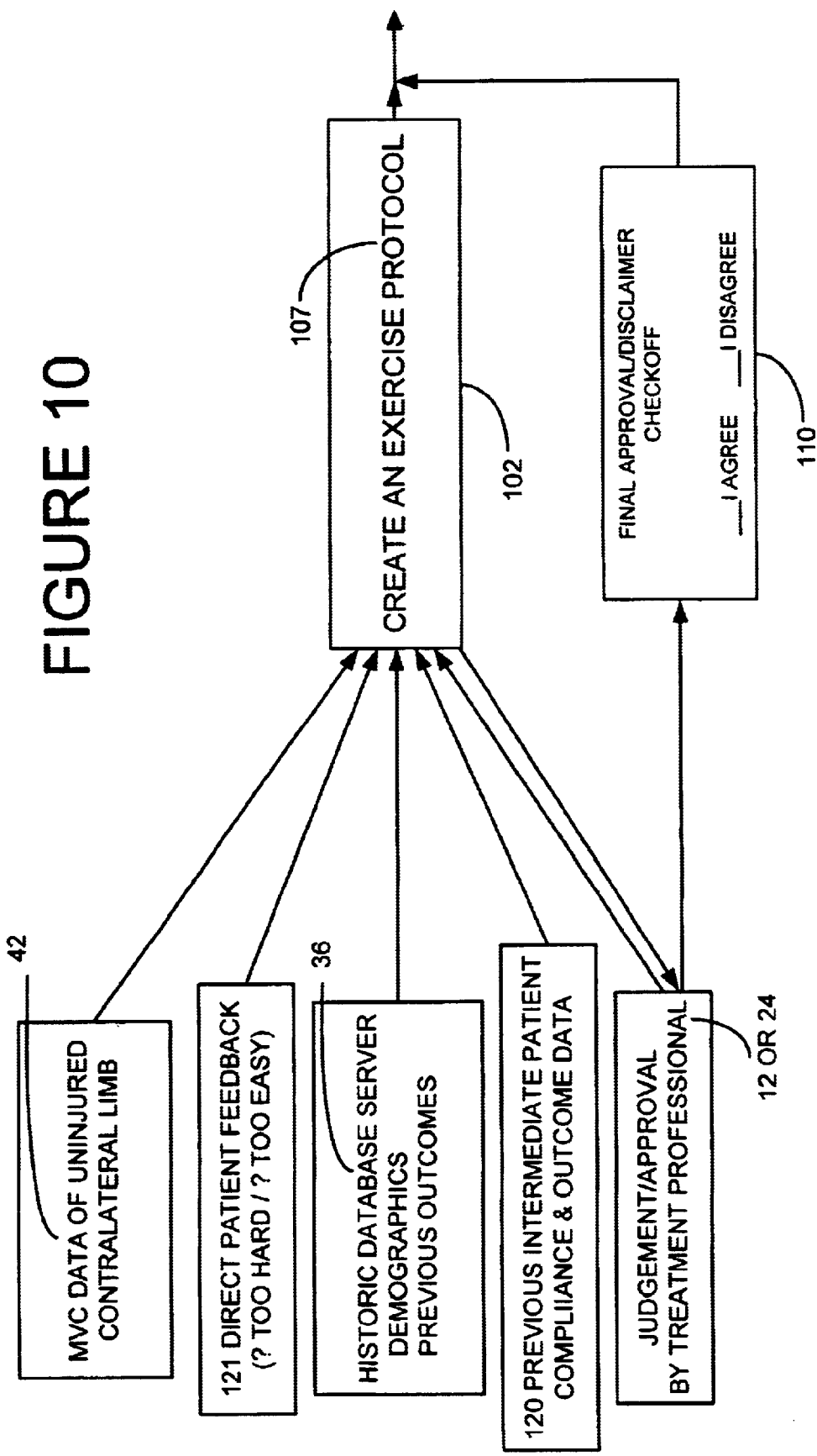
Figure 14:
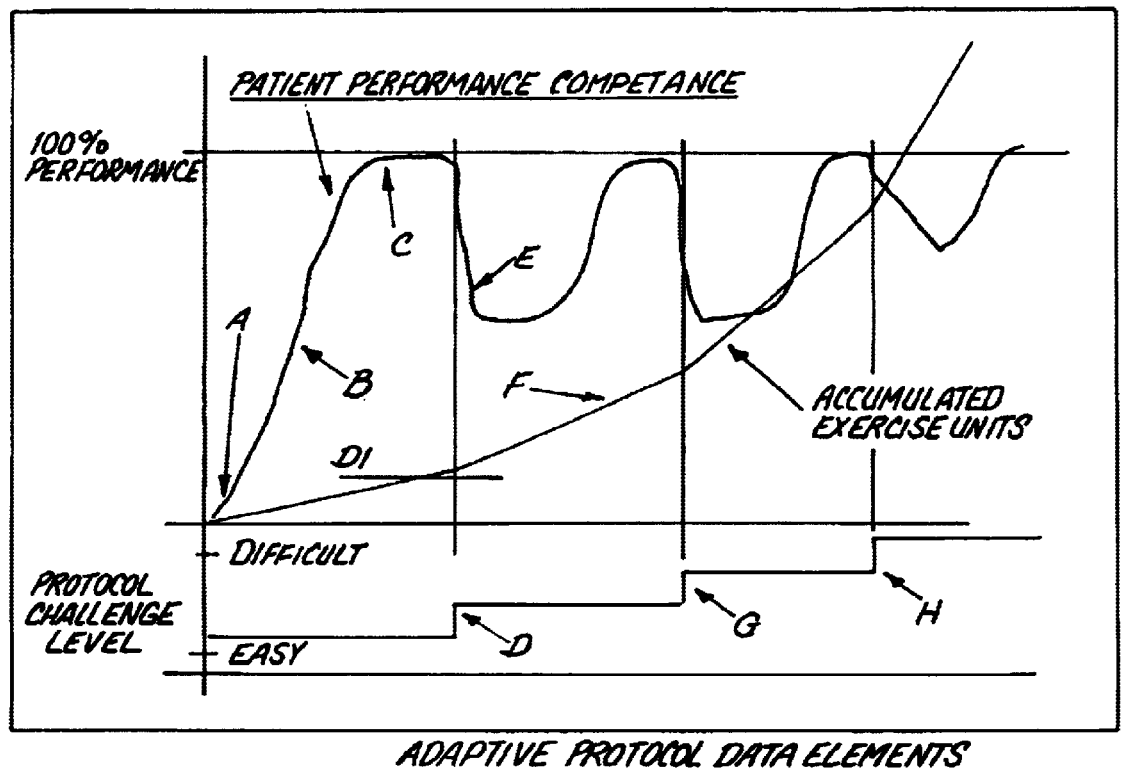
Figure 15:
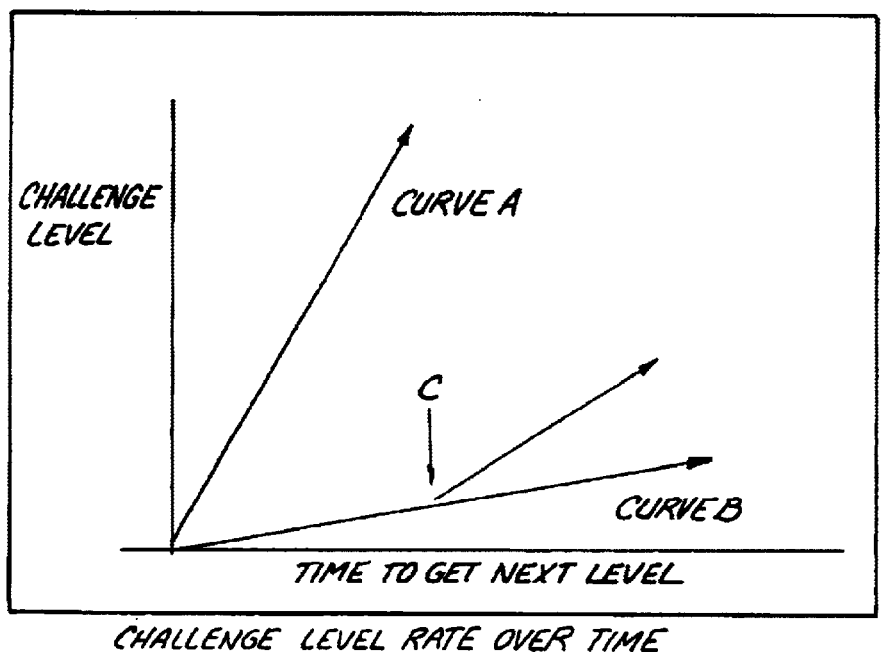

FIG. 7 is a schematic diagram of the relationship between multiple patients and multiple treating professionals, as process participants, and schematically indicating equipment and participants in a treatment system according to still another embodiment of the present invention; FIG. 8 is a schematic diagram of another embodiment of the present invention involving data storage and use of data from an historic database in an embodiment of the present invention;

FIG. 9 is a schematic of information processing systems within the present invention in order to effect treatment of an orthopedic injury, through operations such as data generation, collection, signaling, analysis, modification, review and reporting;

FIG. 10 is a more detailed view of portions of FIG. 9 concerning creating an exercise protocol;

FIG. 11 is a representative compliance report for a hypothetical patient;

FIG. 12 is a set of representative patient recovery reports for a hypothetical patient, with FIG. 12A presenting range of motion plotted against exercise session number, FIG. 12B presenting strength plotted against exercise session number, FIG. 12C presenting fine motor recovery plotted against exercise session number, and FIG. 12D presenting neuromotor and muscular hits plotted against exercise session number;

FIG. 13 is a representive recovery goal analysis for a hypothetical patient;

FIG. 14 is a representative graphical presentation report for a hypothetical patient being treated with a protocol modified three times to be more difficult and showing patient progress after each modification or intervention; and FIG. 15 is a representive set of multiple challenge levels A,B, and C for protocol modification.

SUMMARY OF THE INVENTION

The present invention is a system for treating an orthopedic injury. In a first embodiment, the system includes a definition of a protocol for biological manipulation to be performed upon a patient with an orthopedic injury to be treated according to a coordinated, monitored recovery scheme; a monitoring device, which might be a personal orthopedic restraining device appropriately equipped with a transducer, portable and attachable to a patient with an orthopedic injury to be treated, for monitoring patient activity relative to the protocol or alternatively, a non-restraining monitoring device such as a Therabelt; a portable or more preferably a handheld computer or a palmtop computer; a central processor or computer, segregated from the portable computer, the central computer including a file server, a database, memory, processing, display and communications and including means to generate the protocol; a communication system allowing communication between a pair of distinct computers, most particularly the portable and the central computer; and an analysis interaction algorithm, preferably available to or at the central computer.

The system of the invention may also be understood, in one embodiment, in terms of a process or in another embodiment, in terms of an apparatus. Considered as a process, the invention includes the steps of a.) biologically manipulating a patient for coordinated monitored recovery (such monitoring may be either biophysically or computer monitored); b.) providing a monitoring means, such as a transducer equipped personal orthopedic restrainig device (PORD), or alternatively, a transduce equipped belts, such as a Theraband type device to monitor patient performance of protocol exercises; c.) providing a portable computer, preferably a handheld computer, where the handheld computer includes capabilities for memory, processing, display, recording monitored information from the monitoring means (such as a PORD), and data transmission and reception; d.) providing a central processor (segregated from the portable computer), the central computer including a file server, a database, memory, processing, display and communications; e.) communicating between the provided pair of distinct computers; and f.) analyzing monitored data by an analysis interaction algorithm (preferably by the central computer).

Considered as a device, the invention includes a) means for biologically manipulating a patient for coordinated monitored recovery (such monitoring may be either biophysically or computer monitored); b.) a monitoring means, such as a transducer equipped personal orthopedic restraining device (PORD), or alternatively, a transducer equipped belt, such as a Theraband type device to monitor patient performance of protocol exercises; c.) a portable computer, preferably a handheld computer, where the handheld includes capabilities for memory, processing, display, recording monitored information from the monitoring means (such as a PORD), and data transmission and reception. The portable or handheld computer is, at least at some time, in communication with the monitoring means and preferably includes sufficient information concerning the patient's biological manipulation protocol to compare monitored information with the goal protocol information; d.) a central processor or computer (segregated from the portable computer), the central computer including a file server, a database, memory, patient data outcome and compliance processing, display and communications; e.) communication means between the provided pair of distinct computers; and f.) analysis of monitored data by an analysis interaction algorithm (preferably by the central computer or alternatively another computer, distinct from the handheld computer, and most preferably which is in communication with the central computer).

In a preferred embodiment, the earlier mentioned process embodiment further includes steps to generate information about a prescribed protocol for treating the orthopedic injury of a patient. Such generated information may be in the form of a script, which will then be used in a handheld computer and orthosis device combination to treat an orthopedic injury. The additional process steps include: g. presentation of a set of treatment protocols. The set of protocols to be presented includes at least one treatment protocol. The presentation might be on a display screen or a paper printout or similar hardcopy or both. h.) approval of a treatment protocol from among the presented set of treatment protocols. This step is preferably undertaken by a treatment professional employing professional judgement and, generally, the approval is made in light of further information about the treatment protocol which is being approved. i.) capturing information identifying the approved treatment protocol from the set of presented protocols; and j.) generating information from the captured information into a form compatible with a handheld computer adapted for connection to an orthopedic sensor system, wherein the generated information includes parameters of the identified approved treatment protocol. Additionally the method may include e.) communication from the portable monitoring and communication device of information concerning interactions, communication exchange and/or patient exercise; and f.) modification of the treatment protocol; and g.) monitoring the new protocol.

The present invention includes a number of further embodiments. One particularly notable embodiment involves a database of historic information of earlier patients, their injuries, their actual treatments protocols as performed, and resulting outcomes and a communications and data method to connect the two optimizing functions together. New information can be accumulated in such a database while performing the process of certain embodiments of the present invention and information from the database is made available and utilized in other embodiments of the present invention.

The present invention in another embodiment is a system for treating an orthopedic injury. The system includes a handheld computer adapted for connection to an orthopedic sensor system, a central computer including a historic database of orthopedic injuries, patient characteristics, treatment protocols and outcomes. The system allows an inquiry of the database, i.e. the central computer is queried to cause presentation of a set of treatment protocols to a treatment professional. The treatment professional approves a treatment protocol from the set and the system generates formatted parameters corresponding to the approved treatment protocol for installation in the handheld computer. Once installed with such parameters, the handheld computer can mediate the approved treatment protocol when it is connected to the orthopedic sensor system. The system further includes monitoring performance of the patient in response to the treatment protocol and updating the historic database with the monitored performance parameters. The system further includes the possibility for treatment intervention in the form of modification of the formatted treatment protocol parameters in real-time in response to updates to the historic database or in response to patient data recently sent to the computer. Data which is transmitted to the central computer can be analyzed or compared against other databases and sent on for other analysis. When the data is communicated, secure communication schemes may be optionally employed.

DETAILED DISCLOSURE OF PREFERRED EMBODIMENTS

Figure 1:
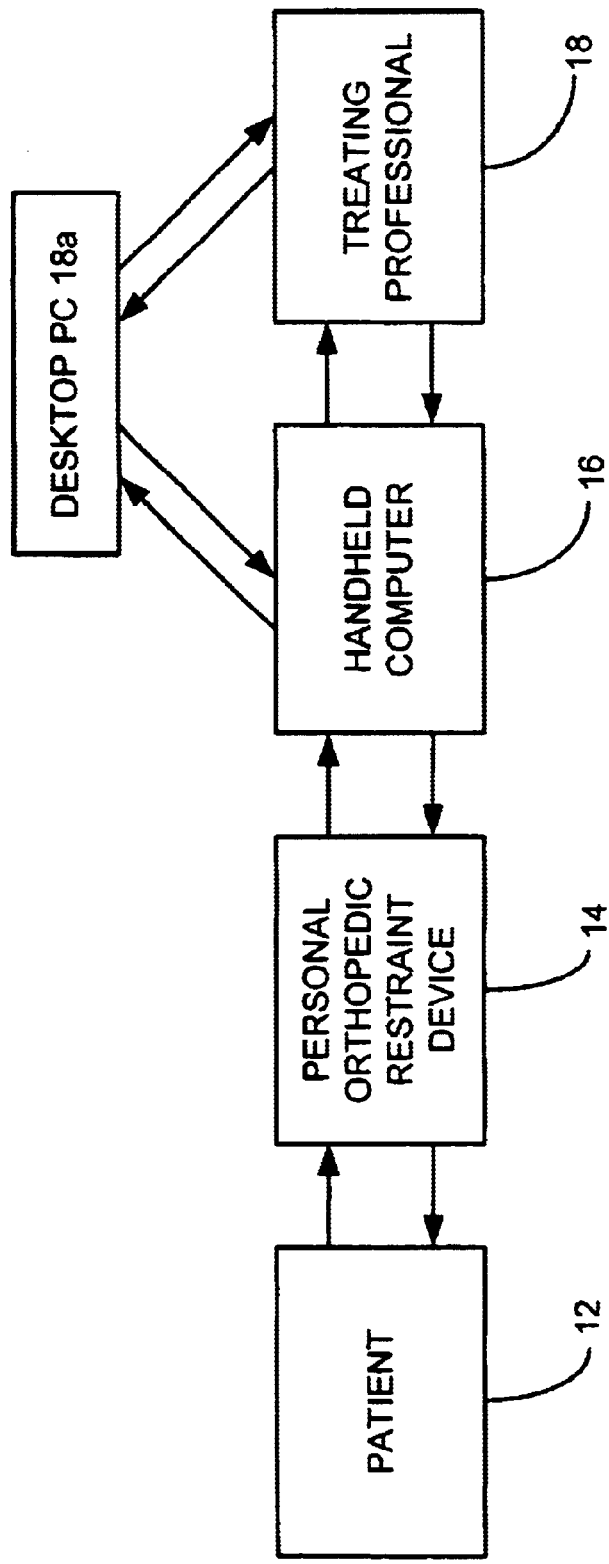
FIG. 1 is a schematic diagram of the relationship between patient and treating professional, as process participants, and schematically indicating equipment of a prior art treatment process.

A background for better understanding of the present invention may be gained by initially considering some earlier innovations developed by one of the inventors. As shown in FIG. 1, treatment of a patient 12 with an orthopedic injury, such as by way of example, an injury at or adjacent the patient's knee, is accomplished by fitting the patient with an orthosis, preferably, a personal orthopedic restraining device (PORD) 14. The PORD 14 serves two important functions. First, it restrains or restricts motion of the patient's leg at the knee to motions consistent with a treatment protocol, and second, it measures a physical parameter of the patient's exercise, such as stress when exercising and knee angle when flexing or extending. The PORD 14 includes a transducer to accomplish such measurement. The transducer of the PORD 14 is connected to a handheld computer 16 which records transducer output signals. The handheld computer 16 is adapted for connection to an orthopedic sensor system. The handheld computer 16 also processes the transducer signals and provides the processed information both directly to an attending treatment professional 18 and to the handheld computer memory for later retrieval. For example, the processed information may be provided as a display on the handheld computer 16. The treatment professional 18 may also install sufficient information in the handheld computer 16 by way of a desktop PC 1 8a to compare the patient's level of compliance with the exercise treatment protocol. An exemplary handheld device such as a SmartIDEA (tm) device is available from IZEX Technologies, Inc., Golden Valley, Minn.

Figure 2:
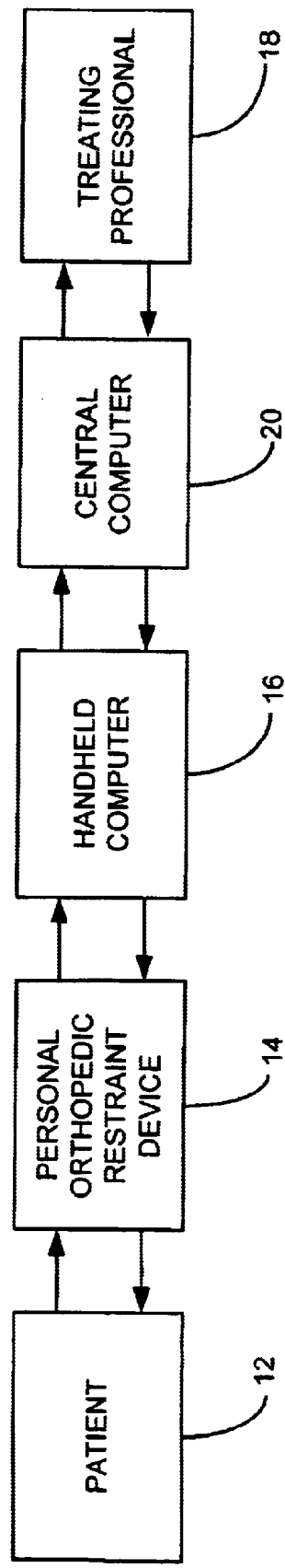
FIG. 2 is a schematic diagram of the relationship between patient and treating professional, as process participants, and schematically indicating equipment used in another prior art treatment process.

As shown in FIG. 2, the handheld computer 16 can also communicate with another computer 20. This second computer 20 may be a central computer 20 segregated from the handheld computer 16, PORD 14 and patient 12 and can process the recorded, preferably preprocessed, information. The communication may be via modem over telephone lines or via cellular radio-telephone transmission. The treatment professional 18 can review the processed results at the central computer 20 location, for example, as a screen display or a hardcopy printout.

Figure 3:
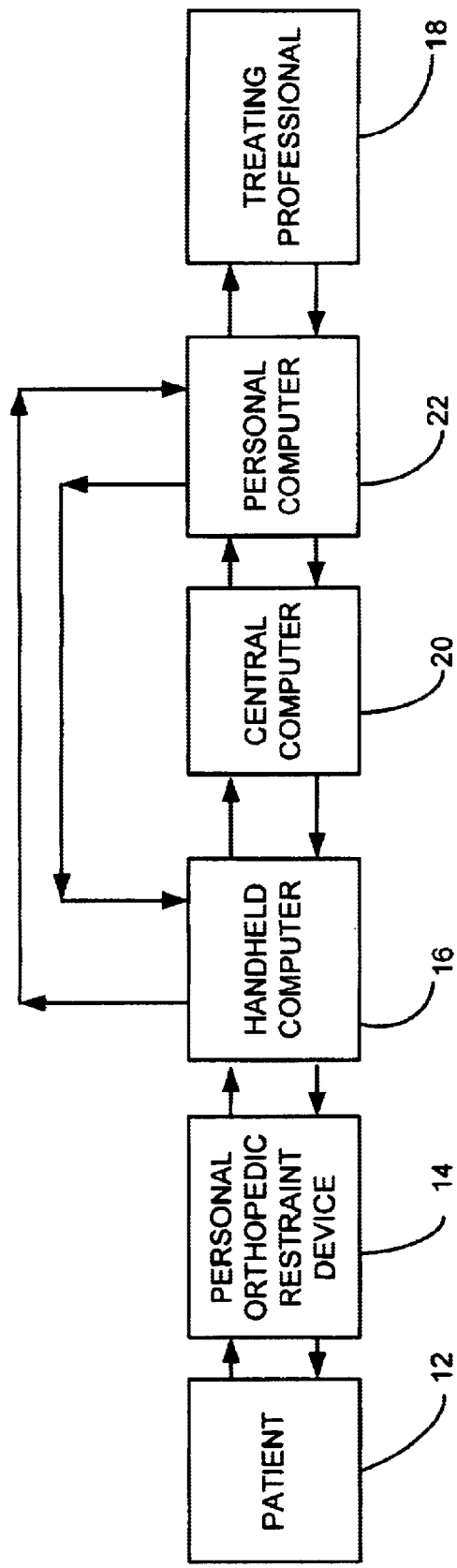
FIG. 3 is a schematic diagram of the relationship between patient and treating professional, as process participants, and schematically indicating equipment used in still another prior art treatment process.

As shown in FIG. 3, the treatment professional 18 may use a personal computer (PC) 22 to communicate with the central computer 20 or directly to the handheld computer 16. The PC 22 may be adjacent the central computer 20 and the communication take place over a serial cable, or it may be remote and use modems over telephone lines. In this system, the treatment professional 18 might send a signal to the handheld computer 16 to tell patient 12 to exercise.

Figure 4:
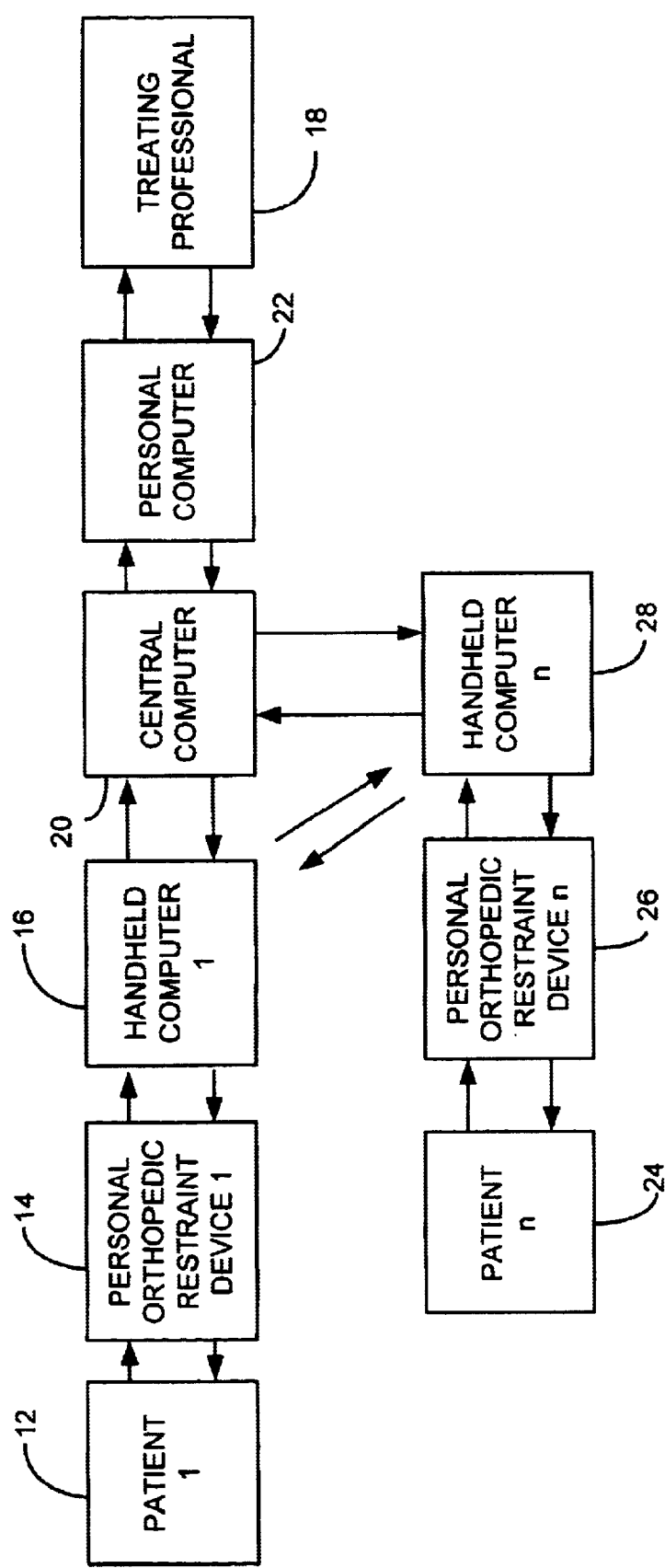
FIG. 4 is a schematic diagram of the relationship between multiple patients and a treating professional, as process participants, and schematically indicating equipment and relationships in a treatment system according to the present invention.

In the present invention, as shown in FIG. 4, the same treatment professional 18, using PC 22, may treat another patient 24 with another PORD 26 communicating with another handheld computer 28 which in turn communicates with the central computer 20. The number of patients 12 and 24 being treated may be expanded and is not limited to only two patients. The handheld computers 16 and 28 may, most preferably, include additional output capabilities selected from the group consisting of RS-232 output, USB output, parallel port output, light output, textual, graphical, audible output, Ethernet input, RF communications output, IR communications output and tactile output.

Figure 5:
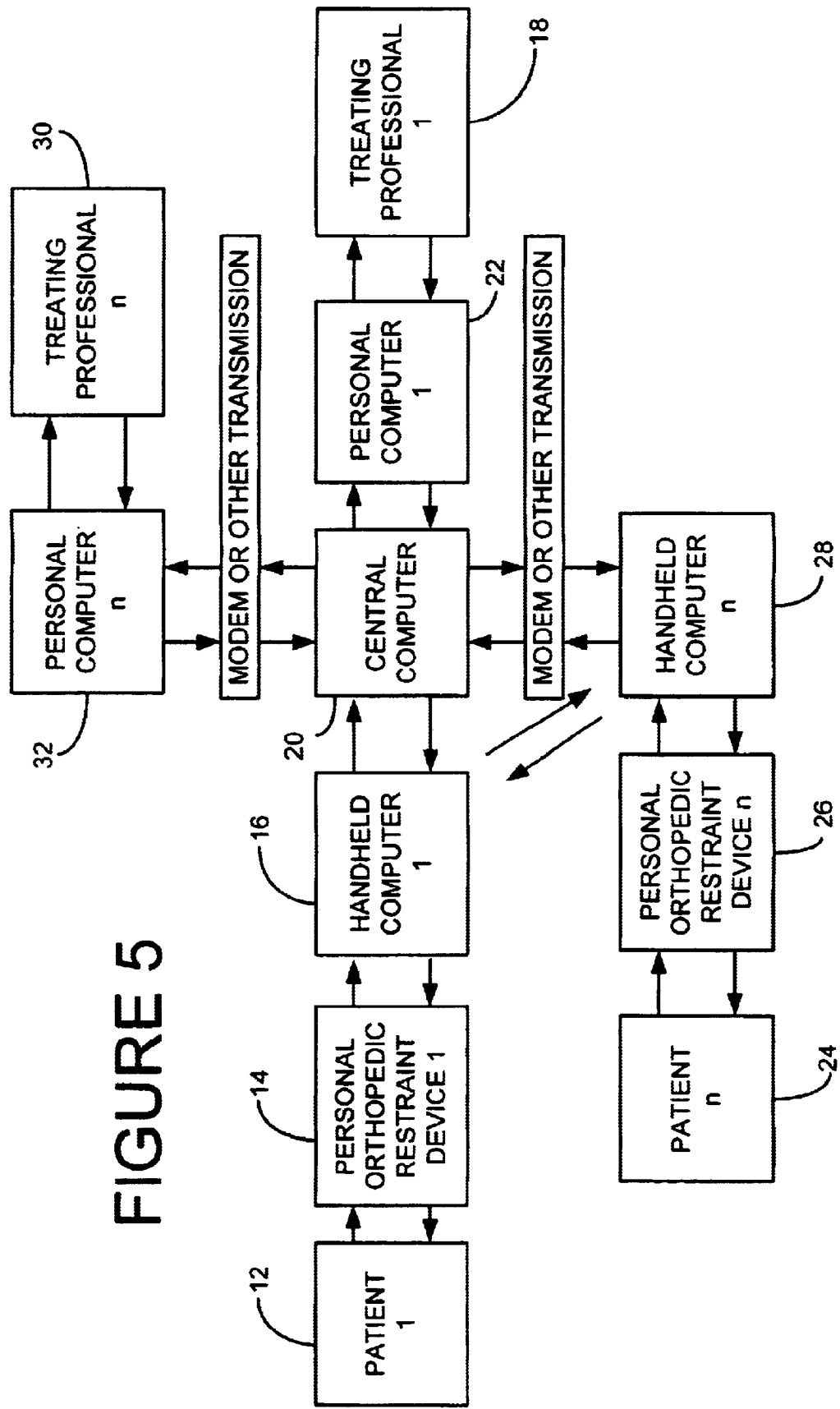
FIG. 5 is a schematic diagram of the relationship between multiple patients and multiple treating professionals, as process participants, and schematically indicating equipment and relationships in a treatment system according to another embodiment of the present invention.

In another embodiment, as shown in FIG. 5, another treatment professional 30, using PC 32, may treat the other patient 24 while the original treatment professional 18 treats the original patient 12. Treatment of the patients 12 and 24 can also be shifted between treatment professionals 18 and 30 as schedules and responsibilities dictate. Alternatively, review, consultation, and related communication between treatment professionals 18 and 30 is possible, and may take place through central computer 20 or by telephone or in face-to-face discussions. The number of patients being treated and/or the number of treatment professionals may be expanded and is not limited to only two.

Figure 6:
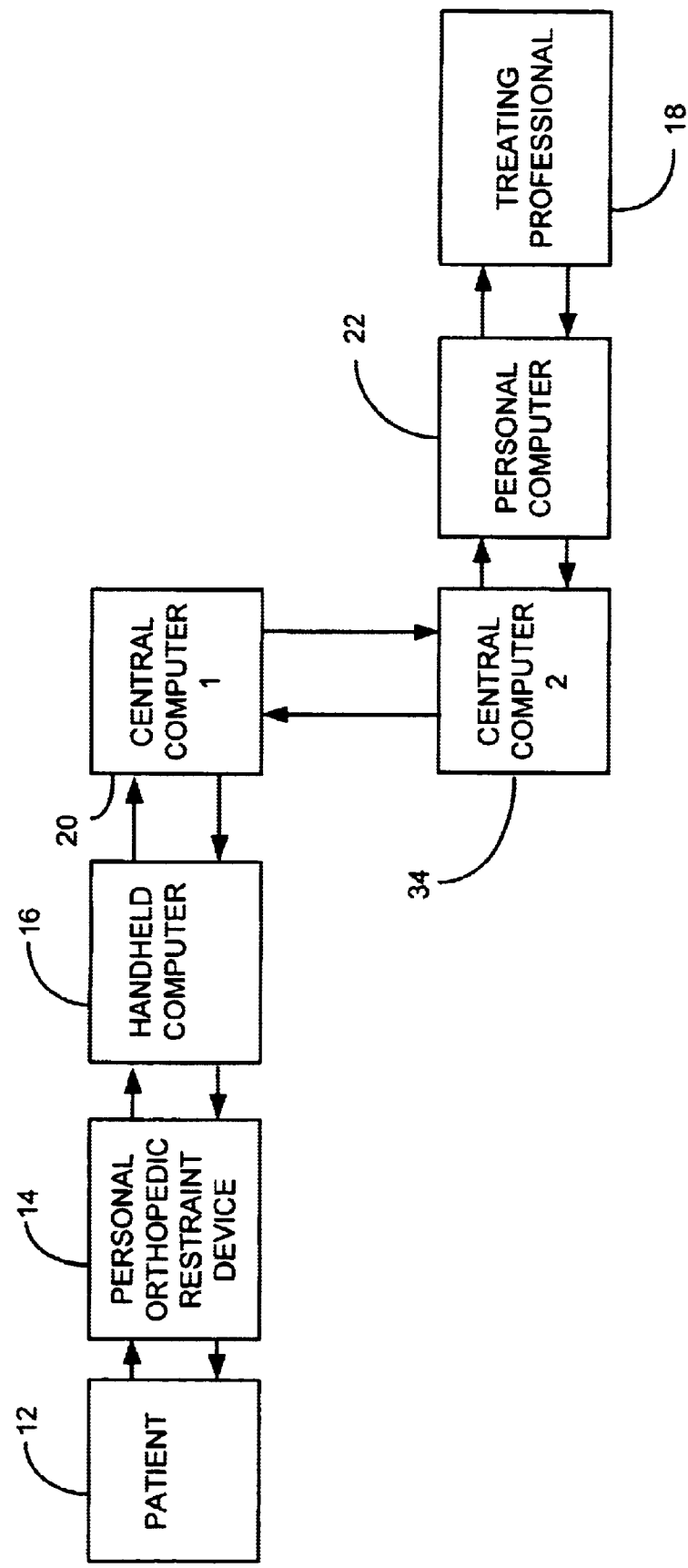
FIG. 6 is a schematic diagram of the relationship between patient and treating professional, as process participants, and schematically indicating equipment and participants as used in a treatment system according to yet another embodiment of the present invention.

In another embodiment, shown in FIG. 6, another central computer 34 communicates with the original central computer 20 and the treatment professional 18 uses original PC 22 to communicate with the another central computer 34 rather than directly with the original central computer 20. Communication between the central computers 20 and 34 may be via modem connections over telephone lines or more preferably over an Internet or intranet network. It should be recognized that the central computer 34 can be one of many central computers on a network, that the network is not limited to only two central computers and that the communications between the two central computers 20 and 34 may be passed through other computers or devices rather than directly between the two computers 20 and 34.

In another embodiment, shown in FIG. 7, the central computer 34 communicates with the original central computer 20 and the treatment professionals 18 and 30 uses original PC 22 and additional PC 32 respectively to communicate with the additional central computer 34 rather than directly with central computer 20. Communication between the central computers 20 and 34 may be via modem connections over telephone lines or more preferably over an Internet, either public or private, or intranet network. Patients 12 and 24 with another PORD 26 communicating with another handheld computer 28 which in turn communicates with the central computer 20. The number of patients being treated may be expanded as may the number of treatment professionals directing treatment. Additionally, attending responsibility for patients may be rotated amongst the treatment professionals. In a variation of this system, any or all of handheld computers 16 and 28 and PCs 22 and 32 may communicate with either central computer 20 or 34 or other like computers on an intranet network or over the Internet. Similarly, the PCs 22 and 32 may connect to other central computers participating in and communicating with the central network. It should also be recognized that either or both of the treating professionals 18 and 30 might be using a networked PC or a workstation of a network.

In a further embodiment of the system of the present invention, a database 36 may be present, as shown schematically in FIG. 8. The database 36 may be present on a central computer 20 or 34 or on another file server in communication with either one or both of the central computers 20 or 34. The use and usefulness of database 36 in the present invention may be further understood in view of some particularly preferred embodiments.

In one such embodiment, treatment protocols can be generated based upon information gleaned from database 36. The database 36 includes a plurality of historic treatment protocol records, the records including fields populated by parameter data for patient characteristics, orthopedic injury, actual treatment protocol followed by the patient, and historic outcome. By "historic treatment protocols" herein is meant actual, accomplished and monitored treatment protocols; and by "historic outcomes" herein is meant the actual, observed recovery or extent of recovery resulting from such "historic treatment protocols." Additionally, in a most particularly preferred embodiment, the database 36 further includes parameter data selected from the group of characteristics consisting of demographics, patient physical characteristics, patient psychological characteristics, and the prescribed protocol provided to the patient. In one variation of this aspect of the present invention, treatment protocols are based upon statistical analysis of data base records. In another variation, the treatment protocols are presented to the treatment professional for review before installing, either all or part, on the handheld computers. That is, the treatment professional is presented with statistical information, such as summaries, means, averages, medians or the like. In a second variation, the treatment professional is presented with at least one or more similar individual case histories. Most preferably, the case history is a database record of a patient or patients with similar characteristics and similar injuries to the patient about be treated. The data from the database 36 which is presented to a treatment professional for approval, is presented either on screen or in printed form or both; and the data may be presented graphically, textually or a combination of both. The data communicated from the handheld computers may also be used to update the historic database 36 with the processed patient compliance information. Use of the data for presentation in order to allow review by a treatment professional or in updating a historic database are not mutually exclusive, and in a most preferred embodiment, the data is used in both ways. It should be understood, that the reviewing treatment professional and the treatment professional involved in the earlier approval step are not necessarily the same individual. Presented data and updated data may additionally be communicated and employed for other uses, such as for example, governmental compliance, insurance purposes, and/or financial reimbursement or employment records. Methods of limiting access to the data in the central computer for confidentiality purposes or financial purposes are, of course, well known, and might include passwords or, in the case of intranets and private access networks, may also include call back modems as security enhancements. Internet data communications may also be made secure using a variety of means including secure socket layers (SSL), encryption, passwords, keys or the like.

Consistent with capabilities of a handheld computer such as, by way of example, the SMART IDEA™ device, the handheld computer may also include patient signaling capabilities selected from the group consisting of audible signaling, visual signaling, and tactile signaling. Similarly, the handheld computer may include input capabilities selected from the group consisting of RS-232 input, sensor signal input, USB input, modem input, keyboard input, audible input, light input, RF input, IR input and Ethernet input. Moreover, the handheld computer may include output capabilities selected from the group consisting of RS-232 output, USB output, parallel port output, light output, textual, graphical, audible output, Ethernet input, tactile and vibrational output. In addition, the handheld computer display may include any number of languages including English, Spanish, and other foreign languages. Also, the displayed graphics may be visual in nature such that non-literate patieints and children may readily understand and use the device.

In one embodiment, the treatment professional 18 or 30 has the initial opportunity to query the database 36 with at least some parameters characteristic of the current patient 12 or 24 and the current patient's orthopedic injury. A query computer program 40, of FIG. 9, is present in the server computer system to query the database 36. This allows the database 36 to be searched for similar case histories in the form of historic records of treatment protocols and outcomes. Alternatively, the query computer program might be used to return statistical information relevant to the patient 12 or 24.

In an extension of these treatment processes, the treatment professional 18 or 30 may modify the initial query, to increase or decrease the number of returned records. Additionally, the historic database 36 may allow queries for predicting the likely outcome of a treatment protocol for a patient 12 or 24 with a particular set of characteristics and a particular orthopedic injury. Using this approach, a treatment professional 18 or 30 can rapidly investigate the efficacy of a range of possible treatment protocols which they might envision for the patient 12 or 24 with a particular orthopedic injury to be treated. Additionally, once at least one treatment protocol is presented, to the treatment professional 18 or 30, they may either modify the presented protocol or the patient characteristics and either re-query the database 36 for likely outcomes or proceed to approve the protocol as indicated in FIG. 10 at 110. It is further provided that the treatment professional may utilize the query program 40 and historical database 36 as part of the treatment system of this invention to simulate an evaluation of a treatment protocol under consideration for a particular patient, then re-modify the treatment protocol based upon the simulation outputs.

It is also part of the present invention that the treatment professional may, in modifying the treatment protocol, select from various pre-recorded sound files, one or more patient directed voice comments, or record one or more individualized, i.e. customized voice comments, for the patient. As mentioned previously, the sound files may be played later for the patient as part of the treatment protocol or conditionally played as part of the treatment protocol. If the handheld computer 16 or 28 includes the capability to play sound files, then the files are played via the handheld computer 16 or 28. Alternatively, the handheld computer 16 or 28 may signal the patient to play the recorded file, for example, by displaying a message on an LCD screen for the patient to do an added motivational or instructional task such as "Listen side #2 cassette recording!" to cause the patient to play an analog cassette recording of reproduced sound selected by or custom recorded by the treatment professional, or alternatively, the patient might be instructed by a displayed message to listen to a sound which is transmitted to the patient over the Internet as a sound file by a message such as "Listen to file PATIENT.WAV!" In another variation of this aspect of the process, the sound files may be provided to the patient as a set of sound files on a device in communication with the handheld computer 16 or 28 such that the device is instructed to play a particular sound file. By way of example, this variation may involve a compact disc recording of one or more sound track files of patient directed comments and a communication link between the hand-held computer 16 or 28 and a compact disc player device, with the ability to be controlled by a handheld computer. Such control might be by a direct wire communication connection or by an infrared signal originated by the handheld computer 16 or 28. The compact disc may be recorded with generic patient directed voice comments or customized comments, such as the treatment professional's voice recording of custom instructions and/or encouragement for the particular patient. In the case of custom instructions, the treatment protocol modification step further includes the treatment professional recording the customized patient instructions, and the generation step, described earlier, further includes the substep of recording the track onto a recordable or rewritable compact disc.

In another embodiment, failure of the patient 12 or 24 to comply with the treatment protocol indicated the necessity of a centrally generated intervention or modification, either with or without presentation to and review by the treatment professional 18 or 30. Failure to comply may include under or over exercise which deviates from the treatment protocol. Alternatively, the monitoring and alerting features (which identify accidents, harmful events, or other incidents of significance in patient exercise) can be used to alert the treatment professional.

In yet another embodiment, a script corresponding to the treatment protocol may further include conditional logic. Most preferably, the conditional logic incorporated within the script serves to further treatment goals; that is, the goal-based conditional logic facilitates a patient's overall treatment program by incorporating the ability for intervention within the script loaded onto the handheld computer. Goal-directed conditional logic, incorporated within the script of the handheld computer might be best understood as a third form of intervention, distinct from both intervention by the treatment professional (which might be driven by non-real time reports or by real time information (such as video) and time-based intervention decisions which are made at a central computer based upon pre-determined time periods. In such an embodiment, the goal-based conditional logic may be used to incorporate the criterion for recognition by the remotely located handheld computer 16 or 26 of a failure of compliance by the patient 12 or 24 and the ability to alter the treatment protocol. For example, goal-based conditional logic could be used to monitor a patient's attempts to meet a particular effort or angle objective to be replicated a set number of times. Detecting that the effort or angle is not being achieved, the goal-based conditional logic might set a new, lower and easier to achieve level of effort or angle and accordingly increase the desired replicate count to at least partially compensate for the easier exercise. Alternatively, the conditional logic may be used to provide criteria for recognition by the remotely located handheld computer 16 or 28 of meeting and satisfying, ahead of schedule, the treatment goal set by the treatment professional as represented by the approved treatment protocol. Those skilled in the art will likely recognize the particular advantages of incorporating goal-based conditional logic within a protocol script loaded on a handheld computer and PORD combination. One such advantage is recognizing accelerated progress toward a treatment goal and responding appropriately by modifying the protocol. In many such cases, the treatment protocol goals may be raised to more challenging levels to better capitalize upon the patient's outstanding efforts. This approach holds the potential to provide a psychological boost to the patient and further allow the motivated patient to progress very rapidly through orthopedic treatment. The alteration of the protocol need not be immediately communicated back to the central computer 20 or 34 but might be saved for later communication Alternatively, the goal-based conditional logic analysis can be carried out at the central computer, with one result being the production of a modification or intervention in the protocol, followed by transmission of the updated protocol from the central computer to the handheld computer.

As shown in FIG. 9, the handling (i.e. the communication and the processing) of information within the system of the present invention can be very complete and yet very efficient in terms of resource utilization. A treatment professional 18 or 30, uses a PC 22 or 32 to access the query program 40 to find protocols from the historic database 36 on a central fileserver. The treatment professional can either create 102 a fresh new protocol , select an appropriate historic protocol or modify parameters of an existing treatment protocol, made up of a group of exercise related parameters. The creation 102 of a treatment protocol is most easily accomplished by using the query program 40 for consultation of database 36.

For example, the treatment professional 18 or 30 sits down at PC 22 or 32 and selects a protocol from a list of historical protocols obtained through query program 40 from historic database 36. Alternatively, a list of protocols may be resident locally at the treatment professional's PC for the same reason. The treatment professional 18 or 30 then optionally modifies parameters of the protocol based upon particular injury details associated with the patient. The resulting modified protocol 107 for the patient is then downloaded 108 via hardwire or wireless communications 112 to the SmartIDEA™ handheld device 16 or 28. The patient 12 or 24, fitted with a PORD 14 or 26, takes the SmartIDEA™ device 16 or 26 home and periodically does exercises, generally according to instructions from the treatment professional 18 or 30 to follow the created protocol 107. As the patient 12 or 24 follows the presented protocol 107, the patient's exercise activity and progress is monitored. The patient is presented with reinforcement signals and instructions based upon comparison of the patient's actual exercise activity to the goals of the protocol 107. The reinforcement signals to the patient may be in the form of visual signals, audible signals, and/or tactile signals, and may include qualitative or quantitative information about insufficient or excessive patient exercise as well as more general motivational signals. After partial completion of the prescribed exercise protocol 107, the recorded data can be communicated (i.e. transmitted) 112 to the central computer server 20 or 34 to generate a progress report 114 for viewing by the treatment professional 18 or 30. The reports can be generated and subsequently presented by a variety of means 116. For example, the presentation of the reports may be via fax, printer, graphic screen display and/or pager display. Transmission 118 of the reports to the treatment professional 18 or 30 may involve hardwire, wireless, Internet or intranet communications. The treatment professional 18 or 30 may respond, after reviewing the reports and exercising judgement about the patient progress, by intervening through revising the protocol 107 to a revised protocol 109 in order to increase the likelihood or rate of achievement of acceptable outcome.

Such an activity pattern can be thought of as a manual intervention. As will be discussed next, however, the system of this invention can provide automatic revision of the protocol, and such automatic intervention or modification may be performed in real-time, if desired.

In another embodiment, this same process of reviewing report compliance and outcome data and revising treatment protocols can be automated through the use of an analysis interaction algorithm which functions for the treatment professional.

More specifically, the analysis interaction algorithm performs two functions (1) analyzing patient performance for reporting or protocol adjustment, (2) automatically adjusting or updating a patient protocol. These two activities are explained as follows:

Patient Compliance to a Prescribed Exercise Schedule.

This portion of the analysis interaction algorithm performs a tally of actual exercises completed, and the actual time of their completion, in comparison to the exercises (goal) which were prescibed and the prescribed schedule for those exercises (goal), as prescribed by the caregiver.

For example, a patient is prescribed an exercise regimen that calls for one exercise per day for 10 days. Upon completion of the 10 day period, data from the handheld device is transferred to the central computer. This portion of the analysis interaction algorithm compares goal and actual schedules and concludes or determines that the patient performed 90 percent of the prescribed exercises. FIG. 11 illustrates one realization of a graphical output of this fast algorithm.

Exercise Performance Compared to Prescribed Challenge Level of Exercises

This portion of the analysis interaction algorithm performs a comparison of patient actual effort expended. This comparison could be based upon measurements from the orthosis sensors in units, such as limb joint angle of flexion/extension or muscle strength measured in units of torque (for example, Ft-lbs). These measured values are compared to the exercise regimen effort goals prescribed by the treatment professional.

For example, a patient is prescribed an exercise regimen that calls for the patient to strive to reach a strength goal of 20 Ft-lbs, as measured by the instrumented orthosis. The patient attempts to reach this goal but can only meet 15 Ft-lbs. This portion of the analysis interaction algorithm compares the goal and actual recorded strength data and concludes or determines that the patient reached 75% of the goal strength exercise regimen. FIG. 12 illustrates one realization of a graphical output of this algorithm.

Exercise Performance Compared to Benchmark Exercise Performance of the Unaffected, Contralateral Limb.

This portion of the analysis interaction algorithm performs a comparison of patient actual effort expended with the injured limb, as explained above, compared to the strength benchmark of the contralateral (uninjured) limb.

For example, a patient prior to rehabilitation therapy has a measurement made on the contralateral limb, and the MVC (Maximum Voluntary Contraction) for that normal limb is found to be 60 Ft-lbs, as measured by an instrumented orthosis. The patient progresses through several weeks of therapy and near the end, is consistently attaining strength levels with the injured limb of 50 Ft-lbs. This portion of the analysis interaction algorithm compares the benchmark and actual recorded strength data and concludes or determines that the patient has regained 83.3% of the contralateral limb MVC strength. FIG. 13 illustrates one realization of an output of this algorithm.

Exercise Performance Compared to Statistical Historical Summaries of Past Comparable Patients.

This portion of the analysis interaction algorithm performs a comparison of patient actual effort and limb recovery levels achieved, at various times in the recovery schedule and in general over the entire duration of the prescribed exercise schedule, with statistical summaries of historical patient data taken from comparable patients with similar injuries and demographic backgrounds.

For example, a patient's overall strength and range of motion performance at weeks 1 through 8 are recorded during the rehabilitation period. To arrive at conclusion or determination about how this patient compares to past patients with the same injuries and using the same (or nearly the same) recovery exercise protocol, this portion of the analysis interaction algorithm compares actual week 1 through week 8 performance of the patient, against data from the historical database, and concludes or determines that the patient has reached 82% overall of the expected levels of strength and recovery, compared to the statistical, historical performance of patients having the same (or nearly the same) injury and demographic background. FIG. 13 illustrates one realization of an output of this algorithm.

Additionally, the algorithm may output data for reports for other use(s), such as insurance company reports to facilitate efficiency of reimbursements and financial controls. No report is shown but such would be customizable based upon the form desired at an insurance organization or other non-medical entity.

Concepts on Protocol/Performance Data Analysis and Feedback:

To further explain and discuss the concepts regarding the closed-loop, goal-based, use of compliance data to make future adjustments to a patient's protocol based upon past performance of the patient, one might consider the follwing. This process can be automated so that as patient performance and compliance data are regularly collected, an algorithm can monitor the data automatically and adjust and produce updated protocols to be sent to the patient which will deliver optimally adjusted levels of exercise challenge, consistent with a number of constraints, including goal-based criteria and safety. Referring then to the FIG. 14, three curves are shown:

1. Patient Performance/Competence/Compliance is a measure of how well the patient is complying with the prescribed exercises. A high score (near 100%) indicates that the patient is doing well and may no longer be significantly challenged at the current Challenge Level.
2. Protocol Challenge Level is a description of the protocol difficulty level. This level should rise in conjunction with injury recovery, but be moderated by safety considerations.

3. Accumulated Exercise Units are the measured, actual amount of work that the patient has achieved. This quantity can be compared to the expected amount of work that the patient should achieve, assuming a given (for example, 80%) level of average compliance. Discussion of operation:

The patient starts out (point A, FIG. 14) just after surgery/injury with an easy exercise protocol. At first, the patient performance is low, but it steadily rises (B) as swelling and pain reduce, and strength is regained. At some point (C) the patient is mastering the current level of challenge (performance levels near 100%) associated with the protocol.

Recognizing that this goal has been reached, the protocol adjustment algorithm increases the challenge level (D) of the protocol, possibly requiring as well that a minimum required number of exercise units (D1) be logged by the patient. In response to this change, patient performance falls below 100% (E) as the patient now finds greater challenge, and a corresponding effort increase required to meet goals. At the same time, the accumulated work units are now rising at a faster rate (F) since for each minute of exercise, the patient must now exert more work to meet the protocol goals presented to him, than he had to with the previous, easier challenge level.

This pattern repeats itself (G, H) as the protocol adjustment algorithm continues to sense patient performance, and as a result adapt (modify or adjust) the protocol to ever increasing levels of difficulty so as to keep the patient challenged, strengthening faster, and on the road to recovery sooner.

Challenge Level Rates Over Time

Refering to FIG. 15 for the following discussion, the challenge levels used in progressive protocols will depend on a number of factors including but not limited to:

Injury type & grade

Patient demographics (i.e. factors considered include: Athlete, sedentary, etc)

Past performance of the patient during the current episode (high compliance track record or low?)

Safety levels associated with the orthosis

In FIG. 15, Curve A illustrates a protocol challenge level progression (rate) that is aggressive, associated with, for example, an injury that has no biomechanical usage limitations, (i.e. "indestructible" lesions such as an ACL reconstruction, rodded femur, etc). In these cases the recovery protocol can be as aggressive as is tolerable by the patient.

Curve B in contrast would be associated with a more gradual progression in challenge level over time, as would be appropriate with vulnerable lesions that cannot safely tolerate a rapid increase in limb/joint re-use. Examples are a meniscus repair, cartilage implant, or similar. A variation in rate ( C ) might be associated with injuries which require low-level, early protocol therapy, but that will tolerate, at some point, a switch to a more aggressive protocol.

For the class of "indestructible" lesions where the exercise protocol challenge level (Curve A) can be as aggressive as possible, it may turn out the most effective protocols are the ones in which patient motivation is highest. In this case, the protocols which have the most interesting, attention-holding and compelling game-theory elements will reveal themselves. These protocols will have the effect of making the patient want to reach goals despite pain and fatigue barriers (of course, always subject to safety constraints) leading to a more rapid return to normal function.

The intervention, in the form of revised protocol 109, is communicated back to the patient's handheld device 14 or 26 (similar to earlier communication (i.e. transmission) 108), which in turn, presents or communicates to the patient 12 or 24 signals about the revised protocol 109.

In another embodiment, the treatment professional 18 or 30 may employ real-time patient interaction 115 via video/audio communications. Such real-time communications 115 include but are not limited to video, audio, telephone, facsimile, wireless (radio, cellular-telephone, television) communications. Alternatively, the treatment professional 18 or 30 may employ other interaction means 117 to provide encouragement to the patient. The patient, thereby, would be provided with guidance and motivational encouragement to attempt, and hopefully complete, the exercise protocol. Such other interaction means include but are not limited to TENS, muscle, audible, visual, palpable, animation and video signals.

Upon completion 119 of the entire prescribed course of treatment, the treatment professional 18 or 30 may view reports 120 and view a final report 122. As described earlier, the reports 120 and 122 may be presented in a variety of ways and communicated or transmitted in a variety of ways 112 126. For example, report presentations may be, but are not limited to fax, printer, graphic screen display or pager display. Communication or transmission of report data may involve hardwire, wireless, facsimile transmission, Internet or intranet communications. The reports may be sent on demand or may be sent automatically based upon a predetermined schedule.

Further detail of the portions of the protocol creation step are shown in FIG. 10. A treatment professional 18 or 30 is presented by the query program 40 with at least one and possibly a plurality of historic protocols from the historic protocol database 36. The query program 40 uses prior patient parameters, such as demographic information and previous outcomes, in the database 36 to select protocols most nearly similar to the query information input by the treatment professional 18 or 30 about the patient to be treated 12 or 24. Alternatively, the query prgram 40 may access the historical database 36, both of which can reside on the treatment professional's local PC rather than on a central computer. The relevant patient injury characteristics from prior patients are also present in the database 36 and in the treating professional's query for the current patient.

A second source of highly relevant patient information is available in many cases in the form of performance information, particularly in the form of a measurement such as the maximum voluntary contraction (MVC), as available from the patient's uninjured contralateral limb. By way of further explanation, the patient's opposite, uninjured limb is presumptively normal and therefore has performance which can provide an approximate and appropriate performance goal or target to be achieved by treatment of the injured limb. In another embodiment of the present invention, a treatment professional may measure the MVC of a patient's uninjured contralateral limb by employing a personal orthopedic restraining device in communication with a handheld computer. This embodiment may be summarized as a process for pre-assessing an orthopedic patient with a limb injury by employing a personal orthopedic restraining device to measure the condition of a presumptively normal contralateral limb. Preferably, the personal orthopedic restraining device is in communication with a handheld computer and most preferably both devices are the same units that will be subsequently utilized in treatment of the patient's orthopedic injury. One of ordinary skill will recognize that a personal orthopedic restraining device is capable of measuring other relevant parameters of the contralateral limb, for example, angle of joint bending.

In another embodiment of the present invention, when the MVC of the uninjured contralateral limb has been measured, the MVC, or alternatively, an appropriate lower value, such as for example 95% of the uninjured contralateral MVC, is set as a treatment goal for the injured limb. More preferably, at least one of these values, i.e. measured MVC of the contralateral limb or proposed MVC goal, are compared to demographic MVC values in the historic database. This comparison can be employed to avoid accepting measurement errors and/or to assess the patient's condition relative to demographic norms. In such a situation, communications are appropriate and it is preferred to employ communications through the Internet to a query program thereby obtaining information from the historic protocol database.

As indicated in FIG. 10, the contralateral MVC and/or proposed treatment MVC data 42 may be used in conjunction with protocols provided from the historic database 36 to create an exercise protocol 107. In the treatment exercise protocol creation process step 102, the treatment professional 12 or 24 interacts with the possible protocols from the historic database 36 and may modify the protocols until an exercise protocol 107 is acceptable. The treatment professional 12 or 24 then provides a final approval by actively selecting an agreement portion 110 to allow the exercise protocol 107 to become available for download to the handheld computer 16 or 28. In addition, the treatment professional may update a protocol 107 based upon recent patient performance data 120 or direct patient feedback or comments 121 which is obtained at anytime between the start of patient treatment and the end of patient treatment In another embodiment, the present invention further facilitates patient recovery outcomes by producing execise protocols which incorporate improved patient motivational aspects. In particular, patient motivation can be improved by reducing tedium and better holding the patient's attention. This can be accomplished by making the exercise protocols appear as a game to the patient. This is particularly suitable for patients who are children and can also serve a readily learned interface for patients who are illiterate. In this embodiment, the personal orthopedic retraining device (PORD) functions as a "joystick" or game control device which is in turn in communication with the handheld computer (Smart IDEA). The handheld computer functions as a pre-processor, modulator, or signal conditioner of game-like information from the PORD. The conditioned or modulated information is communicated to a central or base computer, preferably, via the Internet or by modems over a telephone line or by other methods described earlier. In order to better understand this embodiment, it may be helpful to envision such well-known computerized toys/games as those available from "SEGA" or "PlayStation" in which a player/participant moves a joystick or presses buttons to interact with the game and, in particular, the visual display of the game which is typically represented as a interesting virtual adventure. The handheld computer (for example, a Smart Idea) with an LCD display can be set up to pass outputs into the base computer via keyboard daisy chain, and the base computer (preferably via an Internet web site) can be used to generate the sophisticated graphics and present the data as an attractive, stimulating and even fun display for the patient. Programming can be provided that includes regimens that, instead of, by way of example, are separately numbered exercises #1, #2, & #3, are innovative and in particular integrate all of the actions in a more interesting way.

For example, a indicia on a video screen visible to the patient, such as the "Super Mario" figure or other character representation with which a child patient may readily identify, goes out into the world, he encounters a (virtual) dragon or similar virutal hazard that he must (virtually) jump over, which the child patient can only do by (actually) extending his leg to 5 degrees of flexion. Then the child patient has to push against a (virtual) rock to get it out of the path, which requires an (actual) isometric flexion/contraction at 45 degrees of 15 foot pounds. Next, the child patient who is the game participant has to ring a (virtual) gong by kicking a (virtual) ball, which is accomplished by the child patieint doing another (actual) isometric in extension at 23 Foot pounds. Then the child patient who is a game particiapnat has to grab a (virtual) paddle and swat away the angry (virtual) bumblebees, in a manner that can resemble a "pong" proprioception game. In other words, the exercises of the protocol do not have to be static, repetious, and/or boring for the patieint, since the computer can present the intructions for the protocol exercises, as a game-like activity, and further can randomly alter the order, mix, add entertaining visual and sound information to the patient (i.e. flash, pow, and interesting graphics). Such presentations would be similar to those are previously known and available with the superior processing capability of the game base stations.

In a further embodiment, multiple patients, particularly for example two child patients undergoing orthopedic rehabilitation, can play their protocol performances against each other over the Internet. In such a system, each of the child patients must be identified to the central computer to allow the computer to provide "gaming" consistent with their individually presecribed treatment protocols. The central computer can also handicap the players to keep the game interesting to each of the multiple players. A "base station" Internet site can have the capability to randomly create these routines real-time, and even vary the routines for patients to facilitate recovery from orthopedic injuries through innovative treatment protocols.

Although the present invention has been described with reference to preferred embodiments, workers skilled in the art will recognize that changes may be made in form and detail without departing from the spirit and scope of the invention.

What is claimed is:

1. A treatment control system comprising;
   a) a first computer;
   b) a communication system allowing communication between the first computer and another computer; and
   c) an analysis interaction algorithm performed by the first computer, wherein the analysis interaction algorithm automatically evaluates and updates a patient's treatment protocol.

2. The system of claim 1 wherein the analysis interaction protocol accesses a database of standardized orthopedic treatment protocols and patient outcomes and performs comparisons of potential outcomes for a patient to be treated.

3. The system of claim 2 and wherein the database includes medical literature, historic data on previous patients, and updated data from current patients.

4. The system of claim 1 wherein the analysis interaction algorithm performs real time intervention.

5. The system of claim 1 wherein the communications at system is selected from the group consisting of:
   communications between two servers; communications between two central computers; wireless communications between two microprocessors; communications between a microprocessor and a central computer; and Internet communications.

6. The system of claim 1 and wherein the communications is real time communications and the communications is via telephone lines (POTS).

7. The system of claim 1 and wherein the communications is real time communications and the communications is via Internet.

8. The system of claim 1 wherein the first computer is an ambulatory computer.

9. The system of claim 8 wherein the ambulatory computer is operably connected to a personal orthopedic restraining device adapted for attachment to a patient.

10. The system of claim 9 wherein the personal orthopedic restraining device includes sensors for monitoring patient exercise activity.

11. The system of claim 10 wherein the sensors measure stress.

12. The system of claim 1 wherein the first computer is a central computer.

13. The system of claim 12 wherein the communication system provides for communication between the central computer and an ambulatory computer.

14. The system of claim 1 wherein the automated update by the analysis interaction protocol comprises an increase or decrease of goals in prescribed exercise protocols based on a patient's response to past exercise protocol goals.

15. The system of claim 1 wherein the automated evaluation performed by the analysis interaction algorithm comprises:

a) providing a treatment protocol; and b) comparing a patient's exercise performance with prescribed goals.

16. The system of claim 15 wherein the automated evaluation performed by the analysis interaction algorithm further comprises:

c) comparing a patient's exercise performance with a benchmark; and d) comparing a patient's exercise performance with historic norms.

17. The system of claim 1 wherein the analysis interaction algorithm provides an automated warning to treatment professionals of incidents of significance.

18. The system of claim 1 wherein the treatment protocol administers biological manipulation of a patient.

19. The system of claim 18 wherein the biological manipulation is selected from the group consisting of:

chemical manipulation;

CNS stimulation of peripherally acting hormones (secretogogue);

parenterally administered peripherally acting hormones;

locally administered locally acting hormones;

locally administered drugs; and orally administered drugs.

20. The system of claim 18 wherein the biological manipulation is selected from the group consisting of:

biophysical stimulation;

heat;

vibration;

ultrasound;

electrical current, electromagnetic waves, and;

light.

* * * * *